United States Patent [19]

Veronese et al.

[11] Patent Number: 5,514,572
[45] Date of Patent: May 7, 1996

[54] METHOD TO MAINTAIN THE ACTIVITY IN POLYETHYLENE GLYCOL-MODIFFIED PROTEOLYTIC ENZYMES

[75] Inventors: Francesco Veronese; Paolo Caliceti; Oddone Schiavon, all of Padua; Sartore Luciana, Marano, all of Italy

[73] Assignee: Consiglio Nazionale delle Ricerche, Rome, Italy

[21] Appl. No.: 256,834

[22] PCT Filed: Jan. 29, 1993

[86] PCT No.: PCT/EP93/00205

§ 371 Date: Sep. 19, 1994

§ 102(e) Date: Sep. 19, 1994

[87] PCT Pub. No.: WO93/15189

PCT Pub. Date: Aug. 5, 1993

[30] Foreign Application Priority Data

Jan. 29, 1992 [IT] Italy .................... MI92A0162

[51] Int. Cl.[6] .................... C12N 9/46; C12N 9/68; C12N 9/48; C12N 9/70; C12N 9/76; C12N 9/66; C12N 9/74; C12N 9/72

[52] U.S. Cl. .................... 435/180; 435/212; 435/213; 435/214; 435/215; 435/216; 435/217; 435/218

[58] Field of Search .................... 435/178, 179, 435/188, 212, 213, 214, 215, 216, 217, 180, 218

[56] References Cited

U.S. PATENT DOCUMENTS 4,002,531  1/1977  Royer .................... 435/188
4,495,285  1/1985  Shimizu et al. .................... 435/212
4,610,879  9/1986  Markland et al. .................... 424/94
4,847,325  7/1989  Shadle et al. .................... 525/54.1
5,162,430  11/1992 Rhee et al. .................... 525/54.1
5,219,995  6/1993  Herring et al. .................... 530/381

FOREIGN PATENT DOCUMENTS 2515684  6/1983  France.

OTHER PUBLICATIONS

Trends in Biotechnology, vol. 6, No. 6, Jun. 1988, Cambridge GB, pp. 131–134, "Application of PEG–Enzyme and Magnetite–PEG–Enzyme Conjugates for Biotechnological Processes" by Y. Inada, et al. (see p. 132).

Journal of Bioactive and Compatible Polymers, vol. 8, Jan. 1993, pp. 41–50, "Active Site Protection of Proteolytic Enzymes, by Poly(ethylene glycol) Surface Modification" by P. Caliceti, et al. (see whole document).

Inada et al. (1986) *Trends in Biotechnol*, 4, 190–194.

Primary Examiner—Michael G. Wityshyn
Assistant Examiner—Jon P. Weber
Attorney, Agent, or Firm—Griffin, Butler, Whisenhunt & Kurtossy

[57] ABSTRACT

A method for preparing protease-polyethylene glycol adducts is presented wherein the immobilized reversible inhibitor, benzamidine, prevents reaction of activated polyethylene glycol with the active site of the protease. Improved activity against macromolecular substrates is obtained compared to when the benzamidine is in solution during the conjugation reaction.

5 Claims, 1 Drawing Sheet

METHOD TO MAINTAIN THE ACTIVITY IN POLYETHYLENE GLYCOL-MODIFFIED PROTEOLYTIC ENZYMES

The present invention relates to a method to avoid binding of polyethylene glycol (PEG) at the active site and its surroundings in proteolytic enzymes.

The method, based on the modification reaction of an enzyme-macromolecularized inhibitor complex in the heterogeneous state, allows to obtain enzyme-PEG adducts in which the proteolytic activity toward macromolecular substrates is preserved.

BACKGROUND OF THE INVENTION

The modification of enzymes with polyethylene glycol (PEG) is a technology that has markedly been developed in recent years to obtain adducts having valuable properties for the use both in the biomedical field and as novel biocatalysts, due to the presence of polyethylene glycol chains linked at the surface.

In fact, the enzyme-PEG adducts lose the major part of the typical properties of naturally occurring enzymes, such as immunogenicity and antigenicity, rapid clearance from circulation, easy degradability by proteases and instability in diluted solutions [A. Abuchowski et al., J. B. C., 252 3582, 1977], that often prevent their use in therapy.

In the use of enzymes in biocatalysis, the PEG-enzyme adduct acquires a quite different characteristic, i.e. the solubility in organic solvents, thus allowing a better use of the enzymes in converting liposoluble substrates [Y. Inada et al., Thrends Biotech., 4 190, 1986].

The properties of such novel biotechnologic products are due to the fact that PEG binds to the enzyme surface, thus protruding with its hydraration cloud toward the outer protein solvent, preventing the access of large molecules, such as proteolytic enzymes, as well as the recognition by the immune system. On the other hand, as PEG also has amphyphilic properties, the PEG-enzyme adduct can acquire solubility in organic solvents.

However, the polymeric cloud surrounding the PEG-enzyme adduct also limits the general use of said derivatives: in fact, the enzymatic activity is maintained toward small substrates, that can have access to the active site diffusing among the PEG polymer chains, but it is prevented toward large substrates, that cannot reach the active site due to steric hindrance.

There fore, convenient PEG-enzyme adducts are obtained with enzymes such as superoxide dismutase, catalase, asparaginase, arginase, urease, adenosine deaminase, phenylalanine ammonium liase etc., which are nowadays under pharmacological and clinical tests, but not with enzymes acting on large substrates such as proteins, nucleic acids and polysaccharides. In fact, substantial activity losses are de scribed following a PEG-modification of -trypsin, chymotrypsin, urokinase, ribonuclease, lysozyme and the like.

A proposed solution consists in preparing adducts having only a few polymer chains linked to the enzyme, thus decreasing the loss in enzymatic activity. However, this result, which can be attained carrying out the reaction in a PEG molar defect, suffers from drawbacks such as attainment of very heterogeneous products and poor reproducibility.

SUMMARY OF THE INVENTION

To allow access of macromolecular substrates, large polypeptides or proteins, in case of proteolytic enzymes, to the active site, the PEG binding to the enzyme is carried out in heterogeneous phase, in which the enzyme is linked to an inhibitor thereof that is, in its turn, immobilized on a highly hydrated insoluble polysaccharide (Sepharose). In such a way, the PEG polymer will bind to enzyme areas far form the active site and its proximity, thus allowing the approach of the substrate macromolecules.

The method was investigated with two serine-dependent proteolytic enzymes, trypsin and urokinase, the first being used in medicine, for instance in the removal of necrotic tissues, in digestive disorders or in ophthalmology in the elimination of protein deposits from contact lenses; the latter, i.e. urokinase, being of specific therapeutical interest as a plasminogen activator.

Benzamidine, an inhibitor of serine enzymes, was used as a linker to keep Sepharose in the surrounding of the active site (example 2). The method could also be used for the site-protection of other serine enzymes, such as tissue plasminogen activator (tPA), plasmin, chymotrypsin, elastase, kallikrein and the like.

DESCRIPTION OF PREFERRED EMBODIMENTS

Figure 1:
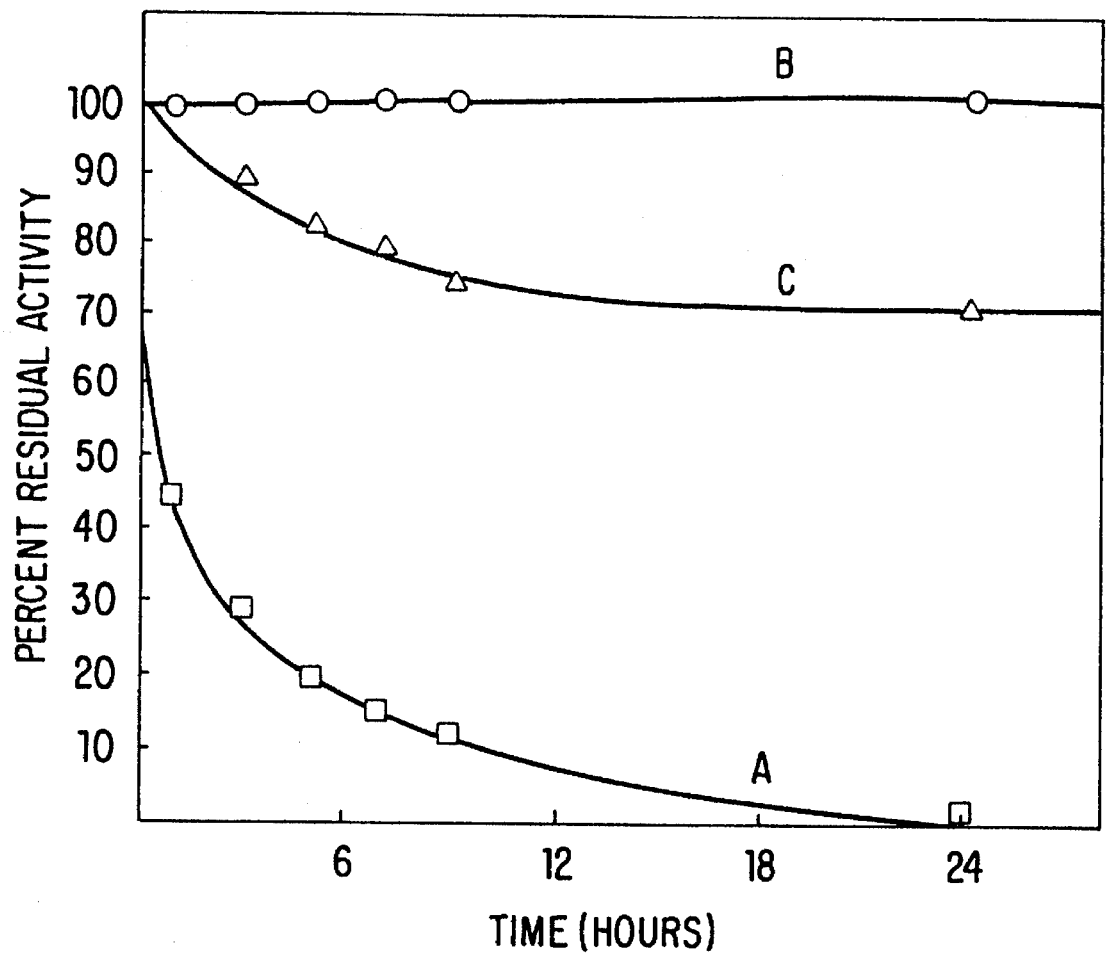
FIG. 1 shows the autolysis of various trypsin samples, evaluated by means of the esterase activity: native trypsin (□), A; PEG-trypsin randomly modified with no site protection or with benzamidine in solution, (O), B; and PEG-trypsin modified in heterogenous phase in the presence of benzamidine-Sepharose, (Δ), C.

The following examples report the comparison of the activities of the starting enzyme A), PEG-modified either with no protection or in the presence of free benzamidine in solution B) and obtained carrying out the modification in heterogeneous phase with the complexed enzyme with the benzamidine-Sepharose macromolecularized inhibitor C) (examples 1, 3, 5, 7).

The obtained results will be described with reference to the figures and tables reported in the following.

In the various modifications, monomethoxypolyethylene glycol of MW 5000 (PEG) was used, bearing norleucine as a spacer between polymer and protein, activated at the carboxy group as the succinimidyl ester. PEG with norleucine was used as it allows a precise evaluation of the linked polymer chains, by means of amino acids analysis [L. Sartore et al., Appl. Biochem. Biotechnol., 27 45, 1991]. Trypsin and urokinase used in the tests were previously purified by affinity chromatography. In the reported examples, the activities of the enzyme various forms (A, B, C) were compared for equimolecular amounts of enzyme, i.e. without taking into account the weigh of the bond polymer.

Table 1 reports the esterase activity toward the small substrate tosyl-arginyl-methyl ester (TAME) of: 1) native trypsin A), trypsin randomly modified with PEG B) and trypsin linked to benzamidine-Sepharose C). In these cases, the catalytic activity is not lost, on the contrary, a small increase in activity occurs in the PEG-modified adducts, which proves that PEG chains do not prevent the access to the active site of a small substrate (example 4). Similar increases in activity have already been observed in proteolytic enzymes, following different chemical modifications.

The same Table also reports the hydrolyric activity toward casein 2a), that is a protein of MW 23,600 turning out to be strongly lowered to about 30%, following a random modification with PEG B), whereas it is totally maintained when the modification is carried out in heterogeneous phase with trypsin linked to benzamidine-Sepharose C) (example 5).

Finally, Table 1 shows that the hydrolyric activity toward bovine serum albumin (BSA) 2b), that is a protein of higher molecular weight, namely 64000, is completely lost in the sample that was PEG-modified in the absence of site-protectors B), whereas a high activity degree is still retained (55% compared with native trypsin) when the modification is performed with trypsin linked to benzamidine-Sepharose C) (example 5).

FIG. 1 shows the autolysis of the various trypsin sample, evaluated by means of the determination of the esterase activity. Trypsin in aqueous solution undergoes degradation very rapidly; when it is randomly modified with PEG B) it does not undergoes self-digestion, whereas the one obtained carrying out the modification in the presence of benzamidine-Sepharose C) shows a slow starting loss of activity, that however becomes stable at about 70%. This behaviour is in agreement with the above results, namely the incapability of randomly modified trypsin B) to digest a large molecule (in the case represented by trypsin itself). The decreased autolysis of the sample modified as a benzamidine-Sepharose complex C) is consistent, on the one hand, with the persistence of the proteolytic activity of this species toward macromolecular substrates, on the other with a more difficult access for proteases, due to steric hindrance of the PEG chains masking the enzyme surface, with the exception of the active site (example 6).

Table 2 reports the properties of native and modified urokinases, measured by means of the esterolytic activity on a small substratum, namely carbobenzoxy lysine-p-nitrophenyl ester 1), the thrombolytic activity on the synthetic thrombus be means of the resistance to penetration of a glass bead 2) and the affinity to the synthetic thrombus by means of colorimetric measurements of thrombus degradation products 3), eventually by the evaluation of the capability to hydrolyse free plasminogen in solution 4).

In this case also samples of native urokinase A), randomly PEG-modified urokinase B) and urokinase modified by site-protection linking urokinase to benzamidine-Sepharose C) were compared.

Table 2 shows that, analogously to trypsin, the activity toward a small substrate increases (example 9).

On the contrary, thrombolytic activity on the synthetic thrombus, measured by means of the resistance to the penetration of a glass bead, disappears in the randomly modified urokinase sample, whereas the samples obtained by site-protection keep a high thrombolytic activity (example 10).

The affinity to a synthetic thrombus decreases of 10 orders of magnitude for sample C (modified in the presence of benzamidine-Sepharose, and of about 500 orders of magnitude for sample B) (obtained by random modification ) ( example 11).

The activity toward plasminogen in solution decreases by one order of magnitude in sample C), and by 2 orders in the randomly modified sample B) (example 12).

Example 1) Preparation of Trypsin-PEG in Conditions of Random Modification 10 mg di trypsin are dissolved in 2 ml di borate buffer 0.2 M, pH 8.0 and added under stirring to 160 mg of activated PEG, to obtain a molar ratio of the amino groups present in the protein to PEG of 1:5, while pH is kept to 8.0 in a pHstat with 0.2 M NaOH. After 30' the solution is diluted with 8 ml of HCl 10 nM and it is ultrafiltered with a membrane of cut-off 10,000 to reduce the volume to 2 ml. The dilution and concentration process is repeated for 5 times. Finally, the solution is purified by gel filtration chromatography and the trypsin-PEG peak is concentrated by ultrafiltration to 2 ml, added again with 8 ml of 10 mM HCl and ultrafiltered repeating the procedure for 5 times. (The modification was carried out also in the presence of benzamidine for an enzyme/benzamidine 1:100 molar ratio and the obtained sample was purified as reported above).

The trypsin-PEG adduct has about 13 PEG chains linked per enzyme molecule.

Example 2 ) Preparation of benzamidine-Sepharose

Sepharose 6B (50 ml) activated by CNBr [P. Cuartecasas, J. B. C., 245 3059, 1970 ] is reacted in borate buffer 0.1 M pH 9.5 with 200 mg of p-aminobenzamidine dissolved in 25% dimethyl formamide 25%. The resin was washed with 25% dimethyl formamide in borate buffer and finally with 0.5 M NaCl, in which it was subsequently preserved. The resin has 5–20 µM of benzamidine per ml. A commercially available benzamidine-Sepharose resin can also be used.

Example 3) Preparation of trypsin-PEG in Conditions of Protection of the Active Site and the Surroundings Thereof 15 mg of trypsin are dissolved in 5 ml of 0.2 M borate buffer, pH 8.0 and added to 5 ml of benzamidine-Sepharose resin, previously washed with 100 ml of 1.5 M NaCl and equilibrated with 0.2 M borate buffer, pH 8.0. After addition of trypsin, the resin is filtered, washed 3 times with 10 ml of 0.2 M borate buffer, pH 8.0 and further filtered.

The resin is added with 5 ml of borate buffer and, under stirring, with 360 mg of activated PEG, to reach a 1:7.5 protein amino groups to PEG molar ratio. The suspension is stirred for 1 hour, filtered and washed 3 times with 10 ml of borate buffer. The trypsin-PEG adduct is removed from the resin by repeated washings (10 times) with 10 ml of 10 nM HCl. The solution is concentrated by ultrafiltration on a membrane and purified by gel filtration chromatography, as in example 1. The trypsin-PEG peak is collected and finally concentrated to 2 ml and diluted with 8 ml of 10 mM HCl and concentrated to 2 ml. This procedure is repeated for 5 times. The modified protein contains about 12 polymer chains per enzyme molecule.

Example 4) Enzymatic Activity of Trypsin and PEG-Trypsin Toward a Low Molecular Weight Substrate This activity is measured using Nα-p-tosyl-arginyl-methyl ester (TAME) as the substrate. The increase in optical density of a solution of 800 µl of 0.046 M Tris HCl, 0.015 M $CaCl_2$ at pH 8.0, 100 µl of 1 mM HCl, 100 µl of a 0.01 M substrate aqueous solution and 0.5 to 6 µg of enzyme.

The activity of the modified products is expressed as a percentage compared to the activity of the native enzyme (Table 1).

Example 5) Activity of Trypsin and PEG-trypsin Toward a High Molecular Weight Substrate To evaluate the protease activity toward high molecular substrates, casein (MW 23000) or serum albumin (MW 64000) were used as standard substrates. A solution of 0.4 ml of 0.1 M Tris HCl, pH 8.0, 0.4 ml of a 1% substrate solution in 0.1 M Tris HCl, pH 8.0 and an enzyme amount from 0.25 to 3 pg is incubated at 30° C. for 20 minutes. This solution is added with 1.2 ml of 5% trichloroacetic acid and the optical density at 280 nm is evaluated on the supernatant after centrifugation and removing of the precipitate. The residual activity of the PEG-trypsin products is evaluated as a percent activity of the native form (Table 1).

Example 6) PEG Autolysis of Trypsin and its Derivatives 0.25 mg of enzyme or PEG-trypsin samples in 1 ml of 0.1 M Tris buffer at pH 8.0 are incubated at 37° C. The esterase activity test is carried out at preset times to evaluate the percentage of still active enzyme

Example 7) Preparation of PEG-urokinase in Random Modification Conditions 2.5 mg of urokinase in 2 ml of 0.2 M borate buffer, pH 8.0, in a polyethylene container, are added under stirring with 30 mg of activated PEG at a protein amino groups to PEG 1:5 molar ratio. After 60 minutes the solution is diluted with 8 ml of 10 mM HCl and concentrated by ultrafiltration. The PEG-urokinase adduct is purified following the procedure of example 1, always working with polyethylene containers. (The modification was carried out also in the presence of benzamidine for a 1:100 urokinase/benzamidine molar ratio and the obtained sample was purified as reported above ). The resulting urokinase has about 14 polymer chains per protein molecule.

Example 8) Preparation of PEG-urokinase in Conditions of Protection of the Active Site and of the Surroundings Thereof 3 mg of urokinase in 3 ml of 0.2 M borate buffer, pH 8.0 are added with 1.5 ml of benzamidine-Sepharose resin, previously washed with 30 ml of 0.5 M NaCl and equilibrated with the same borate buffer. The obtained suspension is added with 72 mg of activated PEG at a protein amino groups to PEG 1:10 molar ratio. After 60 minutes the resin is washed 3 times with 5 ml of 0.2 M borate buffer, pH 8.0 and then the obtained adduct is removed from the resin by washing with 50 ml of 10 mM HCl and purified as in example 3. The obtained adduct has 13 PEG chains covalently linked per enzyme molecule.

Example 9) Urokinase and PEG-urokinase Enzymatic Activities Toward a Low Molecular Weight Substrate This activity is spectrophotometrically evaluated using carbobenzoxy L-Lys -p-nitrophenyl ester hydrochloride (Z-Lys-OpNO$_2$) as the substrate. 65 µl of substrate (2.5 mg/ml of water) are added to 935 µl of 0.1 M K$_2$HPO$_4$/KH$_2$PO$_4$ buffer, pH 6.8 containing 0 to 5 µg of urokinase. The increase in the optical density at 360 nm per minute is reported against the enzyme amounts. The esterase activity of the adducts is expressed as a percentage compared with that of the native enzyme and it is reported in Table 2.

Example 10 ) Urokinase and PEG-urokinase Fibrinolytic Activity Inside a Synthetic Cloth 500µl of a fibrinogen solution (30 µg/ml ) in 0.1 M Na$_2$HPO$_4$/K$_2$HPO$_4$, 0.5% of BSA, pH 7.2, containing 25 to 100 urokinase enzyme Units and finally 100µl of thrombin (500 UI/ml) in 0.1 M KH$_2$PO$_4$/Na$_2$HPO$_4$ buffer pH 7.2 containing 1 mg of BSA are subsequently placed into a glass test tube (9 mm×100 ram). The test tube is turned upside down 2 times and placed into a thermostatized bath at 37° C. After 1 hour, a glass bead of 0.3 g weight is placed onto the formed cloth and the time necessary for the bead to reach the test tube bottom is evaluated The fall time of the bead is reported on a logarithm scale against the corresponding enzyme Units. The fibrinolytic activity, expressed as the percentage compared with standard urokinase of known activity, is reported in Table 2.

Example 11] Urokinase and PEG-urokinase Affinity to a Synthetic Cloth

200 µl of a fibrinogen solution (4.2 mg/ml ) in 0.05 M Tris HCl, 0.15 M NaCl and 0.01 M CaCl$_2$ buffer pH 8.0 and 20 µl of a thrombin solution (500 UI/ml) in 0.1 M Na$_2$HPO$_4$/KH$_2$PO$_4$ buffer, 1% BSA%, pH 7.2, are placed into a test tube. The tubes are centrifuged at 2500 rpm for 20 minutes, to squeeze the cloth that is subsequently extruded, washed with 5 ml of 1.5 M NaCl and dried. The cloth is placed into a cuvette containing urokinase amounts varying from 0.1 to 10 µg 0.05 M Tris HCl, 0.015 M NaCl buffer pH 8.0. Optical Density values, recorded at 3 minutes intervals, are plotted against the time$^2$. The ratio of the concentration of the used enzyme to the obtained slopes is plotted against the urokinase concentration to obtain lines from which the affinity value of the enzyme to the cloth can be evaluated [G.A. Homandberg and T. Wai, Thrombosis Res., 55 493, 1989]. The results are reported in Table 2.

Example 12) Urokinase and PEG-urokinase Activity Toward Plasminogen in Solution In a cuvette containing 900 µl of 0.05 M Tris HCl buffer, 0.15 M NaCl pH 7.0, 50 µl of a solution of 4.41 mg/ml in the same buffer Val-Leu-Lys-pNO$_2$ anilide, 40 µl of a plasminogen 0.125–12.5 mg/ml solution and 10 µl of an urokinase solution or a modified urokinase solution in 0.05 M Tris HCl buffer, 0.15 M NaCl, bovine serum albumin 5 mg/ml pH 7.0. The change in the optical density recorded at 405 nm is plotted against the time$^2$ expressed in minutes, to obtain the plasmin formation rate [V. Eli is et al., J. B. C., 262 14998, 1987]. In Table 2 the enzymatic activities of the various samples are reported.

TABLE 1

Native trypsin and PEG-modified trypsin characteristics

| | Esterolytic activity | Protease activity versus: | |
|---|---|---|---|
| | versus TAME (1) % | casein (2a) % | BSA (2b) % |
| Native trypsin A) | 100 | 100 | 100 |
| PEG-trypsin modified randomly or with an inhibitor in solution B) | 120 | 30 | 0 |
| PEG-trypsin modified by site-protection in heterogeneous phase C) | 115 | 100 | 55 |

(1) Values obtained in Example 4, (2) Values obtained in Example 5.

TABLE 2

| | Native urokinase (UK) and PEG-modified UK characteristics | | | |
|---|---|---|---|---|
| | Activity versus Z-Lys-φpNO$_2$ (1) % | Fibrinolytic activity with UK inside the synthetic thrombus (2) % | Affinity to the synthetic thrombus (3) nM | Activity toward plasminogen (4) Kcat sec$^{-1}$ |
| Native UK A) | 100 | 100 | 2.1 | 25.5 |
| PEG-UK modified randomly or with an inhibitor in solution B) | 115 | 0 | 1079 | 0.5 |
| PEG-UK modified by site-protection in heterogeneous phase C) | 115 | 21 | 24.3 | 2.7 |

(1) Values obtained in Example 9, (2) Values obtained in Example 10.
(3) Values obtained in Example 11, (4) Values obtained in Example 12.

We claim:

1. A method for the preparation of proteolytic enzyme-polyethylene glycol adducts, comprising:

(A) mixing a proteolytic enzyme selected from the group consisting of trypsin, urokinase, tissue plasminogen activator, plasmin, chymotrypsin, elastase and kallikrein with benzamidine which has been immobilized on a hydrated insoluble polysaccharide;

(B) reacting the mixture of (A) with activated polyethylene glycol;

(C) separating the enzyme-polyethylene glycol adduct of (B) from the insoluble polysaccharide; and (D) recovering the enzyme-polyethylene glycol adduct.

2. The method according to claim 1, wherein the reaction occurs in an aqueous suspension buffered with borate to a pH of about 8.

3. The method according to claim 1, wherein the polyethylene glycol is in molar excess of said proteolytic enzyme.

4. The product of the process of claim 1.

5. The product of claim 4, which has activity toward macromolecular substrates.

* * * * *